US010286200B2

(12) United States Patent
Horita et al.

(10) Patent No.: US 10,286,200 B2
(45) Date of Patent: May 14, 2019

(54) SYRINGE AND SYRINGE SET

(71) Applicants: TAISEI KAKO CO., LTD., Osaka-shi, Osaka (JP); FUSO PHARMACEUTICAL INDUSTRIES, LTD., Osaka-shi, Osaka (JP); 3-D MATRIX, LTD., Tokyo (JP)

(72) Inventors: Taiji Horita, Ibaraki (JP); Ippei Matsumoto, Ibaraki (JP); Tomoyuki Sonoyama, Ibaraki (JP); Fukumitsu Nishioka, Osaka (JP); Shoujirou Tanioka, Osaka (JP); Masahiro Nohara, Tokyo (JP); Kiyoshi Takano, Tokyo (JP)

(73) Assignees: TAISEI KAKO CO., LTD., Osaka-shi, Osaka (JP); FUSO PHARMACEUTICAL INDUSTRIES, LTD., Osaka-shi, Osaka (JP); 3-D Matrix, Ltd., Tokyo (JP)

( * ) Notice: Subject to any disclaimer, the term of this patent is extended or adjusted under 35 U.S.C. 154(b) by 294 days.

(21) Appl. No.: 14/915,536

(22) PCT Filed: Aug. 27, 2014

(86) PCT No.: PCT/JP2014/072456
§ 371 (c)(1),
(2) Date: Feb. 29, 2016

(87) PCT Pub. No.: WO2015/030063
PCT Pub. Date: Mar. 5, 2015

(65) Prior Publication Data
US 2016/0213906 A1    Jul. 28, 2016

(30) Foreign Application Priority Data
Sep. 2, 2013   (JP) .................. 2013-181266

(51) Int. Cl.
*A61M 5/31*   (2006.01)
*A61M 5/34*   (2006.01)
*A61M 35/00*  (2006.01)

(52) U.S. Cl.
CPC .......... *A61M 35/003* (2013.01); *A61M 5/345* (2013.01); *A61M 5/347* (2013.01); *A61M 2005/3104* (2013.01)

(58) Field of Classification Search
CPC .... A61M 35/003; A61M 5/345; A61M 5/347; A61M 2005/3104
See application file for complete search history.

(56) References Cited

U.S. PATENT DOCUMENTS 6,821,267 B2 * 11/2004  Veillon, Jr. ........... A61M 39/20
                                                     215/355
2005/0075611 A1   4/2005  Hetzler et al.
(Continued)

FOREIGN PATENT DOCUMENTS

EP       0838229      4/1998
JP    2004-160206 A   6/2004
(Continued)

OTHER PUBLICATIONS

The Extended European Search Report of European Application No. 14840866.9, dated Apr. 7, 2017, 8 pages provided.
(Continued)

*Primary Examiner* — Theodore J Stigell
(74) *Attorney, Agent, or Firm* — Hamre, Schumann, Mueller & Larson, P.C.

(57) ABSTRACT

A syringe and a syringe set are provided. The syringe can be readily distinguished from other syringes only by viewing a tip of the syringe. The syringe includes a tip provided at an end of a barrel body to be filled with a medicine and having an outer diameter of 4.315 mm to 6 mm, a peripheral wall
(Continued)

provided around the tip concentrically with the tip, and a helical rib formed on an inner the of the peripheral wall or an outer face of the tip.

3 Claims, 5 Drawing Sheets

(56) References Cited

U.S. PATENT DOCUMENTS

| | | |
|---|---|---|
| 2006/0106349 A1 | 5/2006 | Kito et al. |
| 2008/0033347 A1 | 2/2008 | D'arrigo et al. |
| 2011/0092918 A1 | 4/2011 | Jensen et al. |
| 2012/0172793 A1 | 7/2012 | Cronenberg et al. |
| 2012/0209216 A1 | 8/2012 | Jensen et al. |
| 2014/0025017 A1 | 1/2014 | Horita et al. |
| 2015/0073390 A1 | 3/2015 | Jensen et al. |

FOREIGN PATENT DOCUMENTS

| | | | |
|---|---|---|---|
| JP | 200798109 | * | 4/2007 |
| JP | 2007098109 | | 4/2007 |
| JP | 2010504106 A | | 2/2010 |
| JP | 2011-72395 A | | 4/2011 |
| JP | 201172395 | * | 4/2011 |
| JP | 2012523932 A | | 10/2012 |
| JP | 2013-507994 A | | 3/2013 |
| WO | 9962577 | | 12/1999 |
| WO | 2012/024370 A1 | | 2/2012 |
| WO | 2012144026 | | 10/2012 |

OTHER PUBLICATIONS

International Search Report issue din PCT/JP2014/072456, dated Oct. 28, 2014.

* cited by examiner

SYRINGE AND SYRINGE SET

TECHNICAL FIELD

The present invention relates to a syringe and syringe set used when a medicine for external application such as a hemostatic is applied or sprayed onto a human body.

BACKGROUND ART

Patent Document 1 discloses a syringe including a nozzle provided on a tip of a barrel body. The nozzle of the syringe includes an outer tube and an inner tube, and a tip of the inner tube protrudes further than a tip of the outer tube.

However, in the syringe disclosed in Patent Document 1, the tip of the inner tube protrudes further than the tip of the outer tube by 1.5 mm at maximum. Thus, such syringe cannot be easily distinguished from other syringes each including an inner tube and an outer tube that are flush with each other merely by viewing the tip of the syringe.

In the syringe disclosed in Patent Document 1, a helical rib having three or more threads is formed on an inner face of the outer tube, and a tip of the helical rib is a flat face. Thus, an object other than a dedicated needle, for example, a general catheter cannot be inserted between the outer tube and the inner tube, and connected thereto.

PRIOR ART DOCUMENT

Patent Document

Patent Document 1: JP 2011-72395 A

SUMMARY OF THE INVENTION

Problems to be Solved by the Invention

The present invention provides a syringe and a syringe set that can be readily distinguished from other syringes only by viewing a tip of the syringe, and can prevent direct connection of injection needles stipulated in ISO594-1 and catheters stipulated in JIS T 3213.

Means for Solving the Problems

A syringe according to the present invention comprises a tip provided at one end of a barrel body to be filled with a medicine, the tip having an outer diameter of 4.315 mm to 6 mm, a peripheral wall provided around the tip concentrically with the tip, and a helical rib formed on an inner face of the peripheral wall or an outer face of the tip.

Since the outer diameter of the outer end 16 is set to 4.315 mm to 6 mm, an injection needle having an inner diameter of 4.0 mm to 4.315 mm, which is stipulated in ISO594-1, cannot be fitted in the tip and, thus cannot be directly connected to the syringe 10. Similarly, a catheter having an inner diameter of more than 6.0 mm, which is stipulated in JIS T 3213, is unsteadily connected to the tip and, thus cannot be directly connected to the syringe. Therefore, the injection needle stipulated in ISO594-1 or the catheter stipulated in JIS T 3213 can be prevented being directly connected to the syringe, eliminating wrong administration of a medicine filled in the syringe via the injection needle or the catheter.

Preferably, a protrusion length of the peripheral wall from the barrel body is smaller than a protrusion length of the tip from the barrel body so that an outer end of the tip is exposed from the peripheral wall in a side view.

Since protrusion lengths of the tip and the peripheral wall from the barrel body differ from each other and the outer end of the tip is exposed from the peripheral wall, the syringe can be distinguished from other syringes in which the tip and the peripheral wall are flush with each other merely by viewing the end of the syringe, preventing wrong administration of a medicine. Further, for example, a nozzle or an adopter can be connected to the barrel body by screwing them to the helical rib.

For example, it is preferable that an exposure length of the outer end of the tip in the side view is 2.1 mm or more.

This arrangement can increase a difference between the protrusion lengths of the tip and the peripheral wall from the barrel body, thereby increasing visibility of the end of the syringe to prevent wrong administration of a medicine more reliably.

Preferably, the helical rib extends from a position corresponding to an outer end of the peripheral wall to a position corresponding to an end of the peripheral wall opposite to the outer end so as to turn around a central axis once.

This arrangement allows that when the nozzle or the adopter is screwed to the barrel body, they can be readily connected to the barrel body merely by rotating them once.

Preferably, a diameter of a crest of the helical rib is 7.83 mm or more.

This arrangement assures that an injection needle having a needle hub with an outer diameter of 7.83 mm, which is stipulated in ISO594-2, is unsteadily connected to the tip 15 and thus, cannot be directly connected to the syringe 10.

A syringe set according to the present invention comprises a syringe including a tip provided at one end of a barrel body filled with a medicine and having an outer diameter of 4.315 mm to 6 mm, a peripheral wall provided around the tip concentrically with the tip, and a helical rib formed on an inner face of the peripheral wall or an outer face of the tip, and a nozzle having an inner diameter conformed with an outer diameter of the tip, the nozzle being to be externally fitted to the tip and connected to the syringe.

As described above, the injection needle or the catheter can be prevented from being directly connected to the syringe, eliminating wrong administration of the medicine filled in the syringe via the injection needle or the catheter. Further, the nozzle can be directly connected to the syringe to apply or spray the medicine via the nozzle. Furthermore, the adopter can be connected to the syringe and the injection needle or the catheter can be connected to the syringe via the adopter.

Effects of the Invention

According to the present invention, a syringe can be readily distinguished from other syringes only by viewing a tip of the syringe, and direct connection of injection needles stipulated in ISO594-1 and catheters stipulated in JIS T312 can be prevented, achieving wrong administration of a medicine.

MODE FOR CARRYING OUT THE INVENTION

An embodiment of the present invention will be described below with reference to appended figures.

Figure 1:
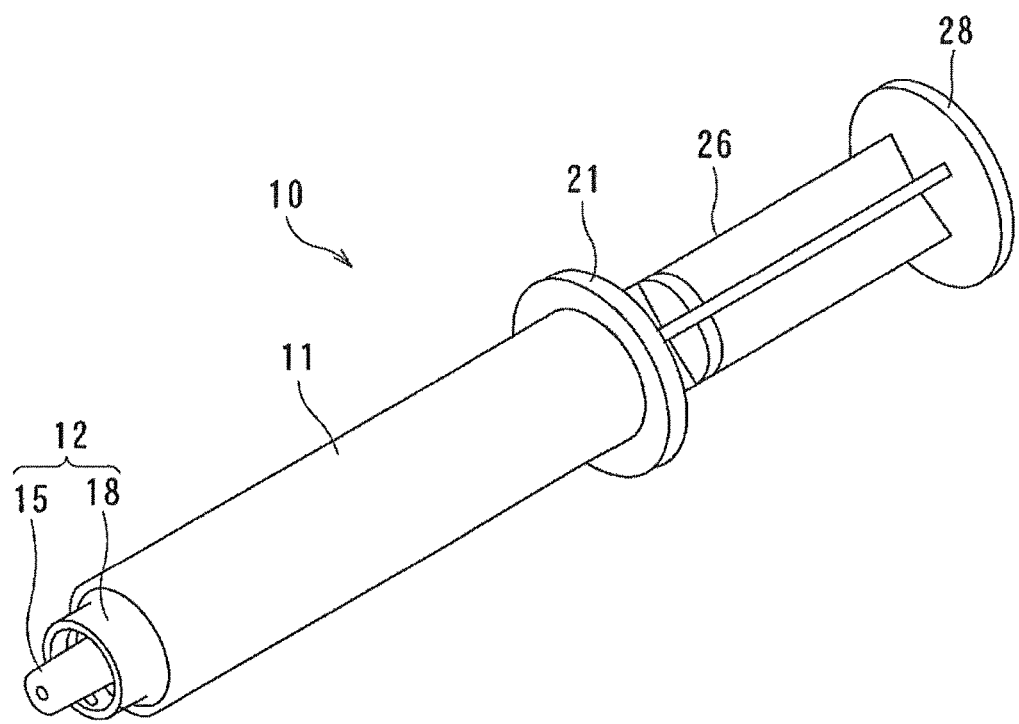
FIG. 1 is a perspective view illustrating a syringe in accordance with an embodiment of the present invention.
Figure 2:
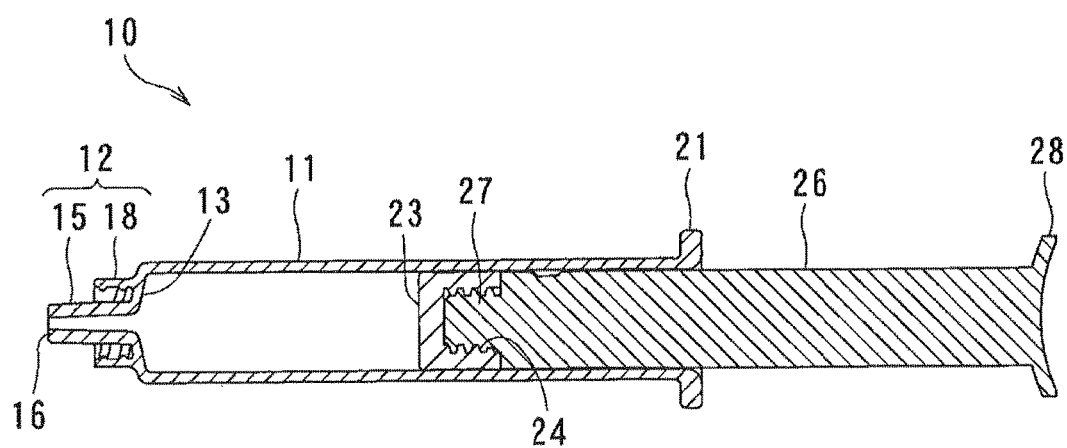
FIG. 2 is a sectional view illustrating the syringe in FIG. 1.

As illustrated in FIG. 1 and FIG. 2, a syringe 10 in accordance with this embodiment includes a barrel body 11 to be filled with medicine, a gasket 23 slidably disposed in the barrel body 11, and a plunger 26 attached to the gasket 23.

The barrel body 11 is a tuboid member made of a transparent or semitransparent resin. The barrel body 11 includes a connecting portion 12 at its one end, and a flange 21 at the other end.

Figure 3:
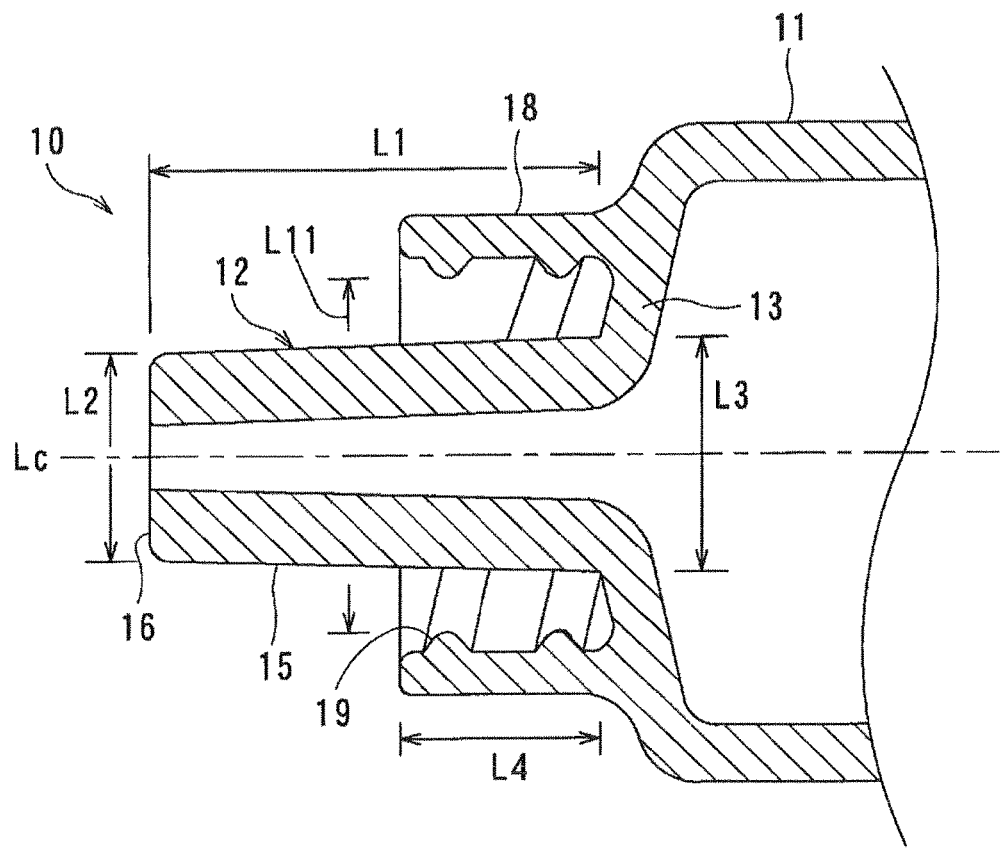
FIG. 3 is an enlarged sectional view illustrating a tip of a syringe body.

The connecting portion 12 is connected to a below-mentioned nozzle 31 or adaptor 41. As illustrated in FIG. 3, the connecting portion 12 is configured of a tip 15 formed at an end 13 of the barrel body 11, and a peripheral wall 18 provided around the tip 15 concentrically with the tip 15.

The tip 15 is a cylindrical member that protrudes outward from the end 13 of the barrel body 11 and extends along a central axis Lc. A protrusion length L1 of the tip 15 from the end 13 of the barrel body 11 is 10.0 mm. An outer face of the tip 15 is tapered so as to gradually reduce in diameter by 6% from the end 13 of the barrel body 11 to an outer end 16.

An outer diameter L2 of the outer end 16 is preferably, 4.315 mm to 6 mm, and is 4.75 mm in this embodiment. Since the outer diameter L2 of the outer end 16 is set to 4.315 mm to 6 mm, an injection needle having an inner diameter of 4.0 mm to 4.315 mm, which is stipulated in ISO594-1, cannot be fitted in the tip 15, and thus cannot be directly connected to the syringe 10. A catheter having an inner diameter of more than 6.0 mm, which is stipulated in JIS T 3213, is unsteadily connected to the tip 15 and, thus cannot be directly connected to the syringe 10. Therefore, the injection needle stipulated in ISO594-1 or the catheter stipulated in JIS T 3213 can be prevented being directly connected to the syringe 10, eliminating wrong administration of a medicine filled in the syringe 10 via the injection needle or the catheter. An outer diameter L3 of an end opposite to the outer end 16 of the tip 15 is preferably, 5.515 mm to 7.2 mm, and is 5.95 mm in this embodiment.

The peripheral wall 18 is a cylindrical body that protrudes outward from the end 13 of the barrel body 11, and extends along the central axis Lc. A protrusion length L4 of the peripheral wall 18 from the end 13 of the barrel body 11 is smaller than the protrusion length L1 of the tip 15 so that the outer end 16 of the tip 15 is exposed to be clearly visible. Therefore, the syringe 10 can be distinguished from other syringes in which the tip and the peripheral wall are flush with each other merely by viewing the end of the syringe 10, preventing wrong administration of a medicine.

The protrusion length L4 of the peripheral wall 18 is 4.47 mm. The protrusion length L1 of the tip 15 is preferably, 1.25 to 5 times larger than the protrusion length L4, and is about 2.24 times in this embodiment. When the protrusion length L1 is smaller than 1.25 times, visibility of the outer end 16 of the tip 15 lowers, and when the protrusion length L1 is larger than 5 times, a luer lock does not work well. A length of exposure of the outer end 16 of the tip 15 from the peripheral wall 18 in a side view, that is, a length found by subtracting the protrusion length L4 of the peripheral wall 18 from the protrusion length L1 of the tip 15 is preferably, 2.1 mm or more. In this embodiment, the length is 5.53 mm. Therefore, a difference between the protrusion length of the tip 15 and the protrusion length of the peripheral wall 18 from the barrel body 11 can be increased to increase visibility of the end of the syringe 10, preventing wrong administration of a medicine more reliably.

A helical rib 19 protruding toward the central axis Lc is formed on an inner face of the peripheral wall 18. The helical rib 19 extends from an outer end of the peripheral wall 18 to an end opposite to the outer end so as to turn around the central axis Lc once. Accordingly, when the below-mentioned nozzle 31 or adaptor 41 is screwed to the barrel body 11 via the helical rib 19, the nozzle 31 or the adaptor 41 can be readily connected to the barrel body 11 merely by rotating the nozzle 31 or the adaptor 41 once. A diameter L11 of a crest of the helical rib 19 (See FIG. 13) is 7.83 mm or more. Thus, an injection needle having a needle hub with an outer diameter of 7.83 mm, which is stipulated in ISO594-2, is unsteadily connected to the tip 15 and thus, cannot be directly connected to the syringe 10.

The flange 21 is shaped like a ring protruding outward in the direction orthogonal to the central axis Lc, from the entire circumference of an end of the barrel body 11 opposite to the tip 15.

The gasket 23 is a tuboid body that is made of an elastic material, for example, and has one closed end. A head 27 of the below-mentioned plunger 26 is screwed to a hollow portion 24 in the gasket 23. With operation of the plunger 26, the gasket 23 axially reciprocates in the barrel body 11 while putting the outer periphery in close contact with the inner face of the barrel body 11.

The plunger 26 is an integrally-molded plate having a crosswise cross-section. The plunger 26 includes a head 27 connected to the hollow portion 24 of the gasket 23 at one end, and a disc-like operating portion 28 formed at the other end. The user manipulates the plunger 26 by holding the operating portion 28 with fingers or the like.

Figure 5:
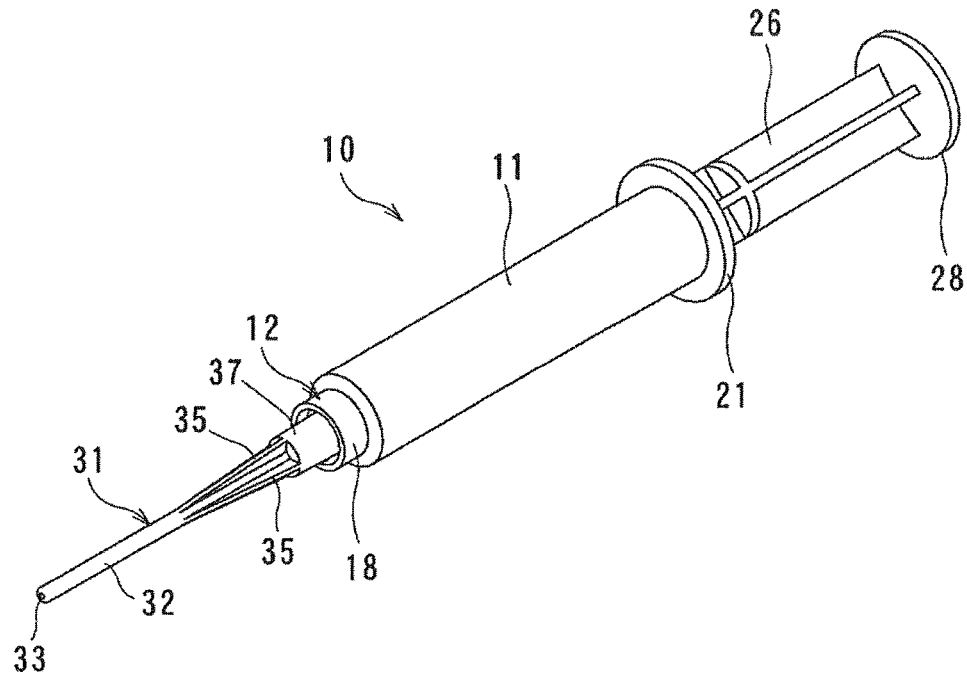
FIG. 5 is a perspective view illustrating the state where the nozzle is connected to the syringe.
Figure 6:
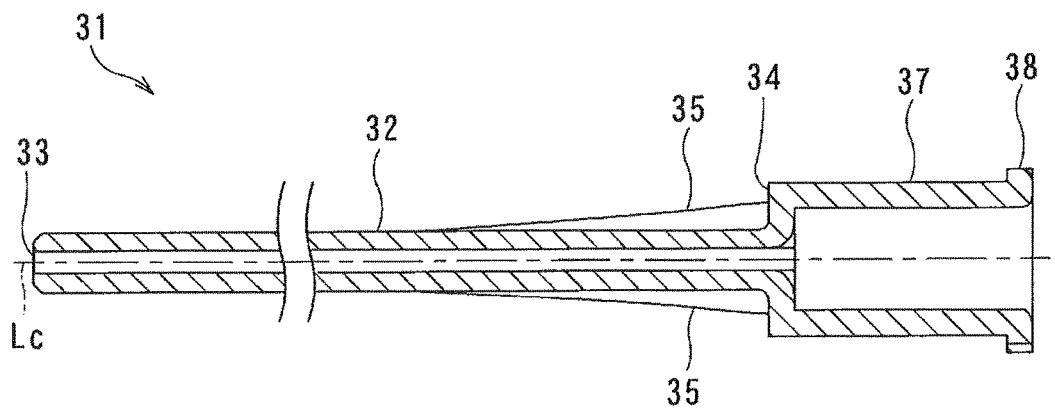
FIG. 6 is a sectional view illustrating the nozzle in FIG. 5.

As illustrated in FIG. 5, the nozzle 31 is connected to the connecting portion 12 of the barrel body 11. The nozzle 31 and the syringe 10 constitute a syringe set. As illustrated in FIG. 6, the nozzle 31 includes a cylindrical nozzle body 32 extending along the central axis Lc, and a connecting portion 37 connected to the nozzle body 32 via a stepped portion 34.

The nozzle body 32 has an opening 33 at an outer end, and the stepped portion 34 at the other end. Ribs 35 inclinedly extending from the almost center of the nozzle body 32 in the longitudinal direction toward the connecting portion 37 is formed on the outer face of the nozzle body 32. The ribs 35 are provided on the outer face of the nozzle body 32 at regular intervals in the circumferential direction. When the nozzle 31 is connected to the syringe 10, a medicine filled in the syringe 10 is applied or sprayed to an affected area through the opening 33.

The connecting portion 37 is a cylindrical member having a larger diameter than the nozzle body 32, and has a jaw 38 at an end opposite to the stepped portion 34. The jaw 38 is shaped like a ring protruding outward from an opening edge of the connecting portion 37 in the direction orthogonal to the central axis Lc. The jaw 38 is screwed to the helical rib 19 of the peripheral wall 18, thereby connecting the nozzle 31 to the syringe 10.

Figure 4:
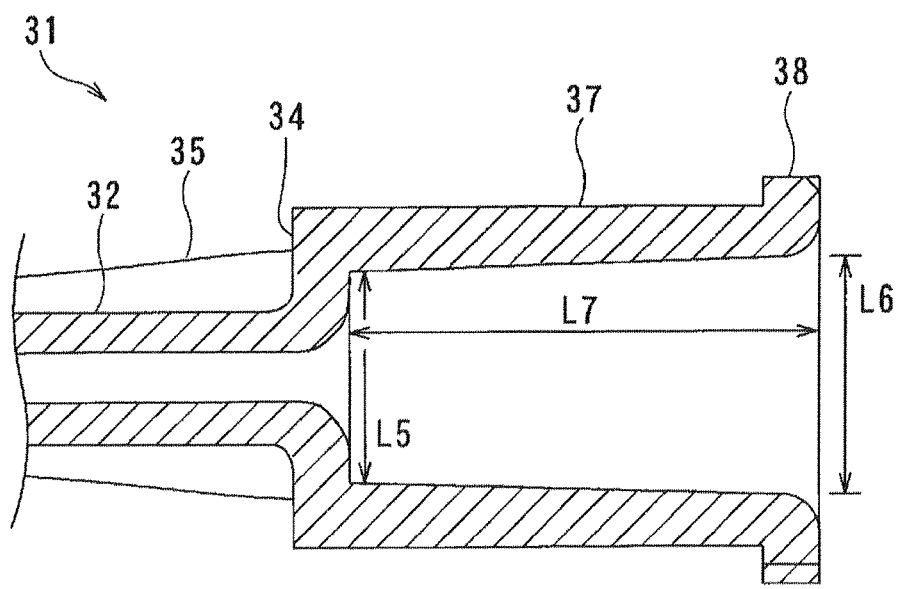
FIG. 4 is an enlarged sectional view illustrating a nozzle connected to the syringe.

As illustrated in FIG. 4, an inner diameter L5 of an end of the connecting portion 37 on the side of the stepped portion 34 is preferably, 3.575 mm to 5.26 mm, and is 4.01 mm in this embodiment. An inner diameter L6 of an opening end of the connecting portion 37 is 5.21 mm, and the inner face of the connecting portion 37 gradually extend in diameter by 6% from the end on the side of the stepped portion 34 toward the opening end. An axial length L7 of the connecting portion 37 on the inner side is 10.0 mm. Since the inner dimensions L5 to L7 of the connecting portion 37 are conformed with the outer dimensions L1 to L3 of the tip 15, the connecting portion 37 can be externally fitted to the tip 15, thereby connecting the nozzle 31 to the syringe 10. The nozzle 31 can be directly connected to the syringe 10 to apply or spray the medicine via the nozzle 31.

Figure 7:
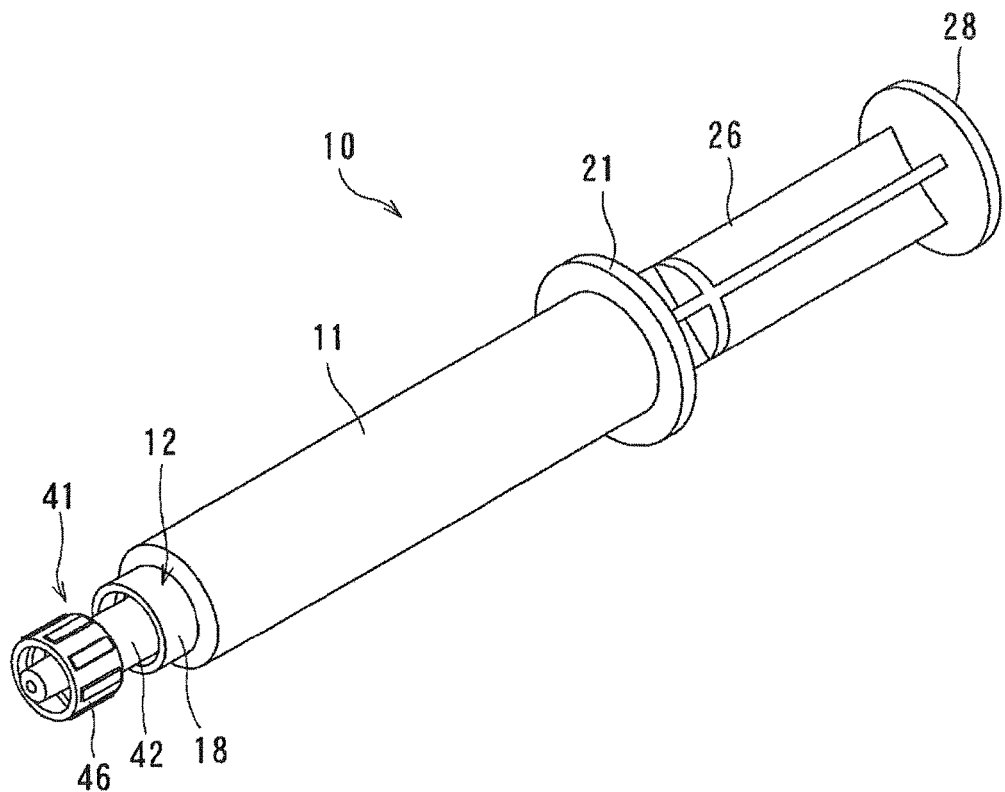
FIG. 7 is a perspective view illustrating the state where an adaptor is connected to the syringe.
Figure 8:
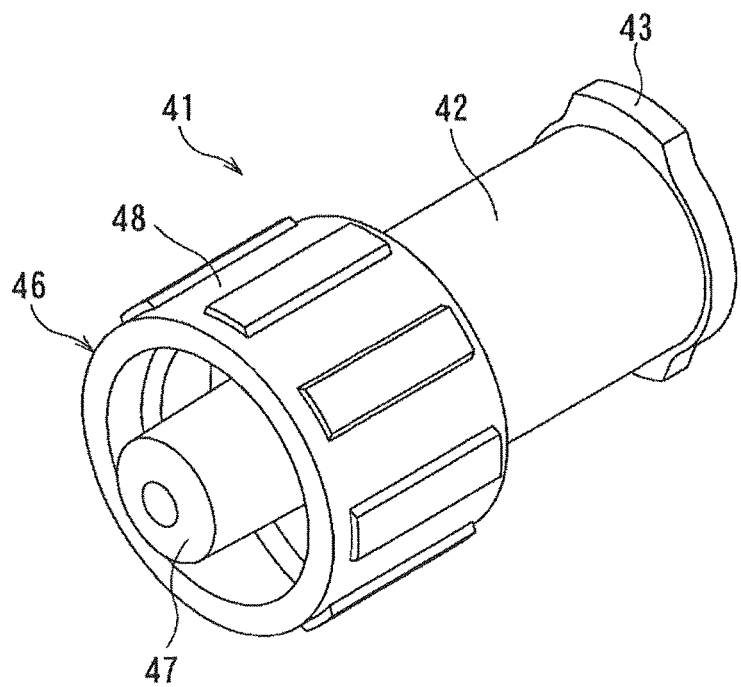
FIG. 8 is a perspective view illustrating the adaptor in FIG. 7.
Figure 9:
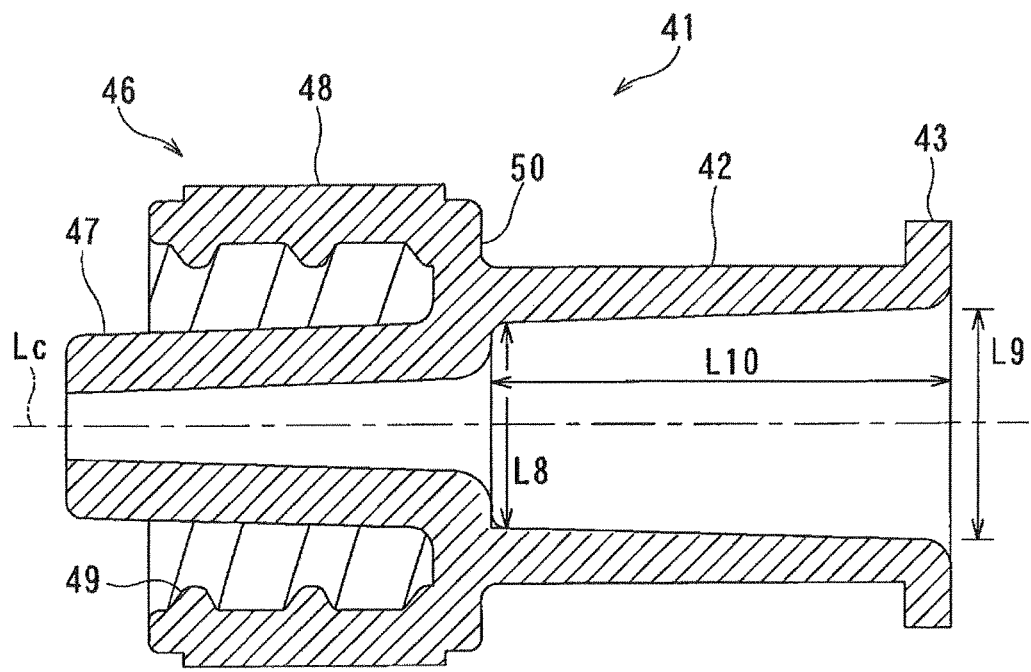
FIG. 9 is a sectional view illustrating the adaptor.

As illustrated in FIG. 7, the adaptor 41 in place of the nozzle 31 may be connected to the connecting portion 12 of the barrel body 11. The adaptor 41 and the syringe 10 constitute a syringe set. As illustrated in FIG. 8 and FIG. 9, the adaptor 41 includes an attachment portion 42 connected to the connecting portion 12 of the barrel body 11, and a catheter connecting portion 46 axially extending from an inner end of the attachment portion 42.

The attachment portion 42 is a cylindrical body that protrudes from a bottom 50 of the catheter connecting portion 46 and extends along the central axis Lc. A pair of protruding pieces 43 protruding outward in the direction orthogonal to the central axis Lc are formed on an opening edge of the attachment portion 42. The protruding pieces 43 are screwed to the helical rib 19 of the peripheral wall 18, thereby connecting the adaptor 41 to the syringe 10.

An inner diameter L8 of an inner end of the attachment portion 42 is preferably, 3.575 mm to 5.26 mm, and is 4.01 mm in this embodiment. An inner diameter L9 of an opening end of the attachment portion 42 is 5.21 mm, and the inner face of the attachment portion 42 gradually extends in diameter by 6% from the end on the side of the stepped portion 34 toward the opening end. An axial length L10 of the attachment portion 42 on the inner side is 10.0 mm. Since the inner dimensions L8 to L10 of the attachment portion 42 are conformed with the outer dimensions L1 to L3 of the tip 15 of the syringe 10, the attachment portion 42 can be externally fitted to the tip 15, thereby connecting the adaptor 41 to the syringe 10.

The catheter connecting portion 46 has a U-like axial cross-section, and includes an inner tube 47, an outer tube 48 provided around the inner tube 47 concentrically with the inner tube 47, and a bottom 50 that connects an end of the inner tube 47 to an end of the outer tube 48.

The inner tube 47 is a cylindrical body extending along the central axis Lc from an inner end of the bottom 50 in the direction opposite to the attachment portion 42. The inner tube 47 is tapered in outer diameter and inner diameter by 6% from the end on the side of the bottom 50 toward the outer end.

The outer tube 48 is a cylindrical body extending along the central axis Lc from an outer end of the bottom 50 in the direction opposite to the attachment portion 42. An axial length of the outer tube 48 is smaller than an axial length of the inner tube 47. A helical rib 49 protruding inward and extending from a tip of the outer tube 48 to the bottom 50 is formed on the inner face of the outer tube 48. A catheter or an injection needle (not illustrated) is screwed to the helical rib 49, thereby connecting the catheter or the injection needle to the adaptor 41. The injection needle or the catheter can be connected to the syringe 10 via the adaptor 41 by connecting the adaptor 41 to the syringe 10.

Figure 10:
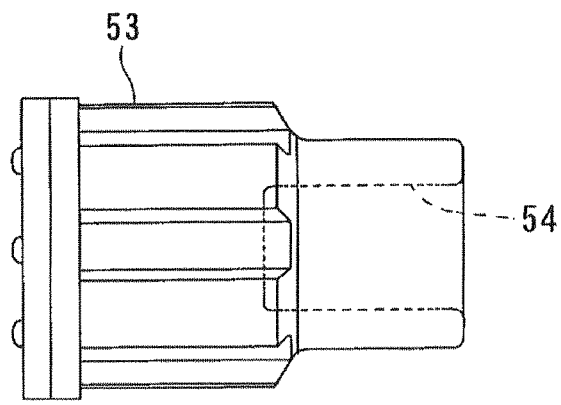
FIG. 10 is a side view illustrating a cap attached to the tip of the syringe.

In the embodiment, to use the syringe 10, the nozzle 31 or the adaptor 41 is connected to the connecting portion 12. However, while the syringe 10 is not used, a cap 53 illustrated in FIG. 10 is attached to the connecting portion 12, preventing foreign matters such as dusts from entering into the syringe 10.

The cap 53 is a tuboid body having one closed end, and includes a cavity 54. The cavity 54 covers the tip 15 of the syringe 10 to attach the cap 53 to the connecting portion 12.

The present invention is not limited to the embodiment, and may be modified in various ways.

The protrusion length L1 of the tip 15 and the protrusion length L4 of the peripheral wall 18 are not limited as long as the syringe 10 can be distinguished from other syringes merely by viewing the tip of the syringe 10. The outer dimensions L2 and L3 of the tip 15 of the syringe 10 are not limited as long as the nozzle 31 and the adaptor 41 can be connected to the tip 15. As a matter of course, the inner dimensions L5 to L7 of the nozzle 31 and the inner dimensions L8 to L10 of the adaptor 41 can be changed according to the dimension of each portion of the syringe 10.

DESCRIPTION OF REFERENCE SIGNS

10 Syringe
11 Barrel body
12 Connecting portion
15 Tip
16 Outer end
18 Peripheral wall
19 Helical rib
31 Nozzle
41 Adaptor

The invention claimed is:

1. A syringe comprising:
a tip provided at one end of a barrel body to be filled with a medicine, the tip having an outer diameter of 4.315 mm to 6 mm;
a peripheral wall provided around the tip concentrically with the tip; and
a helical rib formed on an inner face of the peripheral wall,
wherein a protrusion length of the peripheral wall from the barrel body is smaller than a protrusion length of the tip from the barrel body so that an outer end of the tip is exposed from the peripheral wall in a side view, and
wherein the protrusion length of the tip is 1.25 to 5 times larger than the protrusion length of the peripheral wall,
wherein the helical rib extends from a position corresponding to an outer end of the peripheral wall to a position corresponding to an end of the peripheral wall opposite to the outer end so as to turn around a central axis only once.

2. A syringe set comprising:
a syringe including a tip provided at one end of a barrel body filled with a medicine and having an outer diameter of 4.315 mm to 6 mm, a peripheral wall provided around the tip concentrically with the tip, and a helical rib formed on an inner face of the peripheral wall; and
a nozzle having an inner diameter conformed with an outer diameter of the tip, the nozzle configured to be externally fitted to the tip and connected to the syringe,
wherein a protrusion length of the peripheral wall from the barrel body is smaller than a protrusion length of the tip from the barrel body so that an outer end of the tip is exposed from the peripheral wall in a side view, and wherein the protrusion length of the tip is 1.25 to 5 times larger than the protrusion length of the peripheral wall, wherein the helical rib extends from a position corresponding to an outer end of the peripheral wall to a position corresponding to an end of the peripheral wall opposite to the outer end so as to turn around a central axis only once.

3. The syringe set according to claim 2, further comprising an adaptor having an inner diameter conformed with the outer diameter of the tip, the adaptor configured to be externally fitted to the tip and connected to the syringe.

\* \* \* \* \*